(12) United States Patent
Jang et al.

(10) Patent No.: US 11,351,037 B2
(45) Date of Patent: Jun. 7, 2022

(54) VERTEBRAL BODY IMPLANT

(71) Applicants: INDUSTRIAL TECHNOLOGY RESEARCH INSTITUTE, Hsinchu (TW); NATIONAL TAIWAN UNIVERSITY HOSPITAL, Taipei (TW)

(72) Inventors: Fang-Jie Jang, Keelung (TW); Pei-I Tsai, Hsinchu (TW); De-Yau Lin, Tainan (TW); An-Li Chen, Tainan (TW); Fon-Yih Tsuang, Taipei (TW); Chih-Chieh Huang, Miaoli County (TW); Hsin-Hsin Shen, Hsinchu County (TW)

(73) Assignees: INDUSTRIAL TECHNOLOGY RESEARCH INSTITUTE, Hsinchu (TW); NATIONAL TAIWAN UNIVERSITY HOSPITAL, Taipei (TW)

(*) Notice: Subject to any disclaimer, the term of this patent is extended or adjusted under 35 U.S.C. 154(b) by 1 day.

(21) Appl. No.: 16/730,000

(22) Filed: Dec. 30, 2019

(65) Prior Publication Data
US 2021/0137698 A1  May 13, 2021

(30) Foreign Application Priority Data
Nov. 8, 2019  (TW) .................................. 108140647

(51) Int. Cl.
*A61F 2/44* (2006.01)
*A61F 2/30* (2006.01)

(52) U.S. Cl.
CPC .......... *A61F 2/4425* (2013.01); *A61F 2/4455* (2013.01); *A61F 2002/30133* (2013.01);
(Continued)

(58) Field of Classification Search
CPC combination set(s) only.
See application file for complete search history.

(56) References Cited

U.S. PATENT DOCUMENTS 5,636,518 A * 6/1997 Burgoyne ............... B62L 3/023
60/594
10,130,489 B2  11/2018 McLaughlin et al.
(Continued)

FOREIGN PATENT DOCUMENTS

CN  202051852 U  * 11/2011  ............... A61F 2/44
CN  203988504 U  12/2014
(Continued)

OTHER PUBLICATIONS

TW Office Action in Application No. 108140647 dated May 28, 2020.
(Continued)

*Primary Examiner* — Jennifer Dieterle
*Assistant Examiner* — Danielle A. Stark
(74) *Attorney, Agent, or Firm* — Maschoff Brennan (57) ABSTRACT

The disclosure relates to a vertebral body implant including a flexible main body and at least one pedicle screw joint. The flexible main body is an integrally formed single piece having at least one joint-accommodating hole and at least one opening connected to the at least one joint-accommodating hole. The pedicle screw joint is an integrally formed single piece movably accommodated in the at least one joint-accommodating hole.

10 Claims, 10 Drawing Sheets

(52) U.S. Cl.
CPC ............... *A61F 2002/30578* (2013.01); *A61F 2002/30841* (2013.01); *A61F 2002/30985* (2013.01); *A61F 2310/00017* (2013.01); *A61F 2310/00023* (2013.01); *A61F 2310/00029* (2013.01); *A61F 2310/00179* (2013.01)

(56) References Cited

U.S. PATENT DOCUMENTS

| | | | |
|---|---|---|---|
| 2007/0123990 A1 | 5/2007 | Sharifi-Mehr | |
| 2009/0164019 A1 | 6/2009 | Hsu et al. | |
| 2009/0306719 A1* | 12/2009 | Meyer, III | A61B 17/7005 606/264 |
| 2012/0078307 A1* | 3/2012 | Nihalani | A61B 17/7004 606/264 |
| 2016/0310289 A1* | 10/2016 | Arlet | A61F 2/4455 |

FOREIGN PATENT DOCUMENTS

| | | |
|---|---|---|
| CN | 107530112 A | 1/2018 |
| TW | M314034 U | 12/1995 |
| TW | M398894 U | 3/2011 |
| TW | I383772 B | 2/2013 |
| WO | 2009/055481 A1 | 4/2009 |
| WO | 2015175952 A1 | 11/2015 |
| WO | 2017049268 A1 | 3/2017 |
| WO | 2017190236 A1 | 11/2017 |

OTHER PUBLICATIONS

Lewandrowski et al. "Anterior spinal arthrodesis with structural cortical allografts and instrumentation for spine tumor surgery" SPINE vol. 29, No. 10, pp. 1150-1159; May 15, 2004.

Bridwell et al. "Anterior fresh frozen structural allografts in the thoracic and lumbar spine. Do they work if combined with posterior fusion and instrumentation in adult patients with kyphosis or anterior column defects?" SPINE vol. 20, No. 12, pp. 1410-1418; Jun. 15, 1995.

R. Glennie et al. "A Systematic Review With Consensus Expert Opinion of Best Reconstructive Techniques After Osseous En Bloc Spinal Column Tumor Resection" SPINE vol. 41, No. 20S, pp S205-S211; Oct. 15, 2016.

Viswanathan et al. "Initial experience with the use of an expandable titanium cage as a vertebral body replacement in patients with tumors of the spinal column: a report of 95 patients" Eur Spine J (2012) 21:84-92; Jun. 18, 2011.

Alan D. Aaron "The management of cancer metastatic to bone" JAMA, Oct. 19, 1994—vol. 272, No. 15.

K. Tomita, et al. "Total en bloc spondylectomy for solitary spinal metastases" International Orthopaedics (SICOT) (1994) 18:291-298; Mar. 8, 1994.

K. Tomita, et al. "Total en bloc spondylectomy and circumspinal decompression for solitary spinal metastasis" Paraplegia 32 (1994) 36-46.

Girolami et al. "Biomimetic 3D-printed custom-made prosthesis for anterior column reconstruction in the thoracolumbar spine: a tailored option following en bloc resection for spinal tumors: Preliminary results on a case-series of 13 patients" European Spine Journal (2018) 27:3073-3083; Jul. 23, 2018.

Dvorak et al. "Effectiveness of titanium mesh cylindrical cages in anterior column reconstruction after thoracic and lumbar vertebral body Resection" SPINE vol. 28, No. 9, pp. 902-908; May 1, 2003.

CN Office Action in Application No. 202010000574.4 dated Oct. 11, 2021.

\* cited by examiner

VERTEBRAL BODY IMPLANT

CROSS-REFERENCE TO RELATED APPLICATIONS

This non-provisional application claims priority under 35 U.S.C. § 119(a) on Patent Application No(s). 108140647 filed in R.O.C. Taiwan on Nov. 8, 2019, the entire contents of which are hereby incorporated by reference.

TECHNICAL FIELD

The disclosure relates to an implant, more particularly to a vertebral body implant.

BACKGROUND

Vertebral bone defects may occur due to tumors, degenerative or infectious diseases, or congenital effects, which can ultimately result in the destruction of the vertebral body, resulting in the need for the vertebral body reconstruction. Most reconstructions use a vertebral body replacement (VBR) implant to be placed into the space created by the removal of the vertebral body and disks, and pedicle screws attached to a connection rod can be implanted into the upper and lower vertebral bodies and the vertebral replacement to provide immobilization and stabilization of vertebral segments.

However, the vertebral body implants existing in the current market still have many disadvantages. For example, the conventional vertebral body implants often wear and damage the adjacent areas of the vertebral bodies due to its high rigidity and insufficient flexibility, the damaged vertebral bodies may not be able to maintain the implant and other vertebral bodies in the desired orientation and thus eventually leading to lesion or degeneration.

Also, during daily activities, the vertebral bodies are exposed to significant pressure. Due to the high rigidity and insufficient flexibility of the implant, an undesired stress concentration on the vertebral bodies which are in contact with the implant will occur. For the same reason, the conventional implants are unable to ideally cooperate with the movement of the spine so that it may easily slip out of place, resulting in fusion failure.

In addition, most existing vertebral body implants are shaped in cylindrical form, such that the stress concentration would be mainly applied to the inner soft cancellous bone of the vertebral bodies, which easily causes severe damage to the adjacent vertebral bodies.

SUMMARY

One embodiment of the disclosure provides a vertebral body implant including a flexible main body and at least one pedicle screw joint. The flexible main body is an integrally formed single piece having at least one joint-accommodating hole and at least one opening connected to the at least one joint-accommodating hole. The pedicle screw joint is an integrally formed single piece movably accommodated in the at least one joint-accommodating hole.

BRIEF DESCRIPTION OF THE DRAWINGS

The present disclosure will become better understood from the detailed description given hereinbelow and the accompanying drawings which are given by way of illustration only and thus are not intending to limit the present disclosure and wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details.

In addition, for the purpose of simple illustration, well-known features may be drawn schematically, and some unnecessary details may be omitted from the drawings. And the size or ratio of the features in the drawings of the present disclosure may be exaggerated for illustrative purposes, but the present disclosure is not limited thereto. Note that the actual size and designs of the product manufactured based on the teaching of the present disclosure may also be properly modified according to any actual requirement.

Further, as used herein, the terms "end", "part", "portion" or "area" may be used to describe a technical feature on or between component(s), but the technical feature is not limited by these terms. In addition, unless otherwise specified, the term "substantially", "approximately" or "about" may be used herein to provide an industry-accepted tolerance to its corresponding term without resulting in a change in the basic function of the subject matter at issue.

Furthermore, unless otherwise defined, all the terms used in the disclosure, including technical and scientific terms, have their ordinary meanings that can be understood by those skilled in the art. Moreover, the definitions of the above terms are to be interpreted as being consistent with the technical fields related to the disclosure. Unless specifically defined, these terms are not to be construed as too idealistic or formal meanings.

Figure 1:
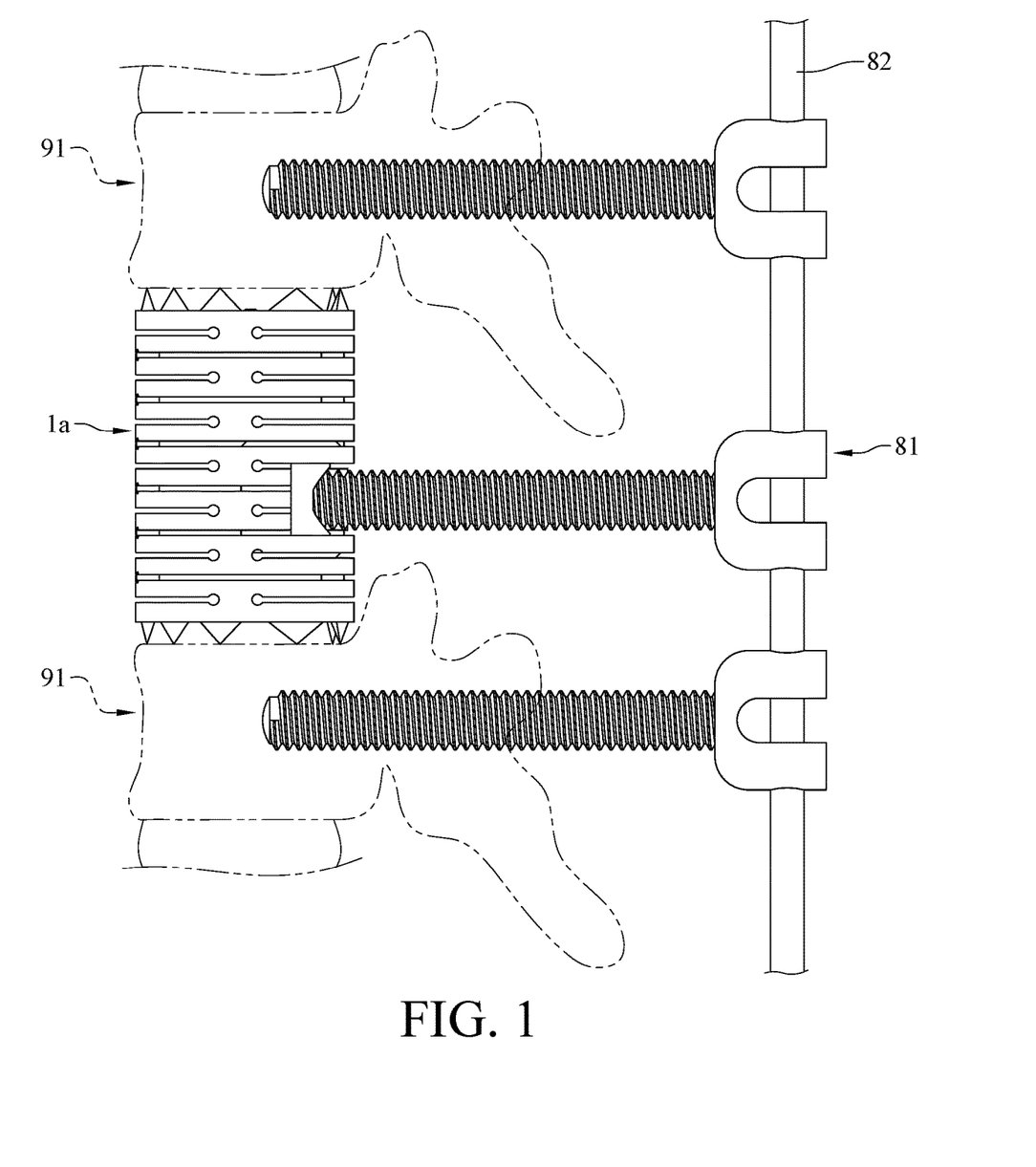
FIG. 1 depicts a scenario that a vertebral body implant according to one embodiment of the disclosure is implanted into a space between adjacent vertebral bodies.

Firstly, please refer to FIG. 1, a vertebral body implant 1a is provided. As shown, the vertebral body implant 1a is configured to be implanted into the space originally occupied by a vertebral body 91; that is, the vertebral body implant 1a is able to replace the removed vertebral body 91. In addition, the vertebral body implant 1a is cooperative with one or more pedicle screws 81 and one or more spine fixation rods 82 to provide immobilization and stabilization of the vertebral body implant 1a and the adjacent vertebral bodies 91.

In this and some other embodiments, the vertebral body implant 1a may be, but not limited to, manufactured by 3D printing technology and its material is biocompatible and has sufficient rigidity to provide proper support to the vertebral body 91 and maintain the desired position of the vertebral body 91, such as titanium alloy, iron-based alloy, cobalt alloy, polymer material, ceramic or composite material thereof, but the disclosure is not limited thereto.

The vertebral body implant 1a is configured for vertebral body fusion. The vertebral body implant 1a is able to provide proper support to the vertebral bodies 91 and maintain the desired position of the vertebral bodies 91. Note that the vertebral body implant 1a may have rough surfaces to aid the fusion process, but these features are omitted from the drawings for the purpose of simple illustration. Also, the vertebral body implant 1a is a multi-directional, flexible, and compressible object to adapt to the movement of the vertebral bodies 91 to prevent itself from slipping out of place and reduce the stress concentration on the adjacent vertebral bodies 91.

Figure 2:
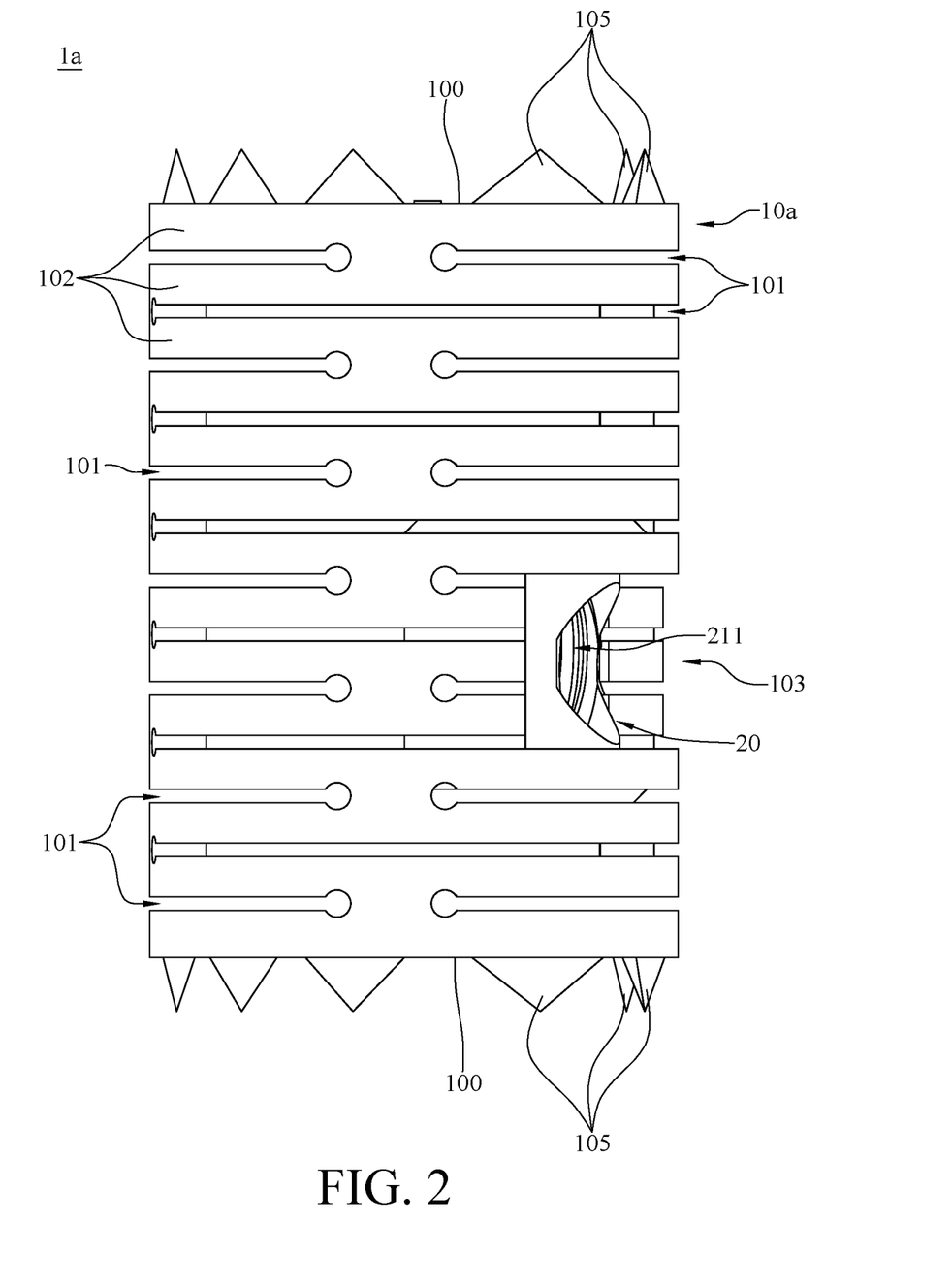
FIG. 2 is a side view of the vertebral body implant in FIG. 1.
Figure 3:
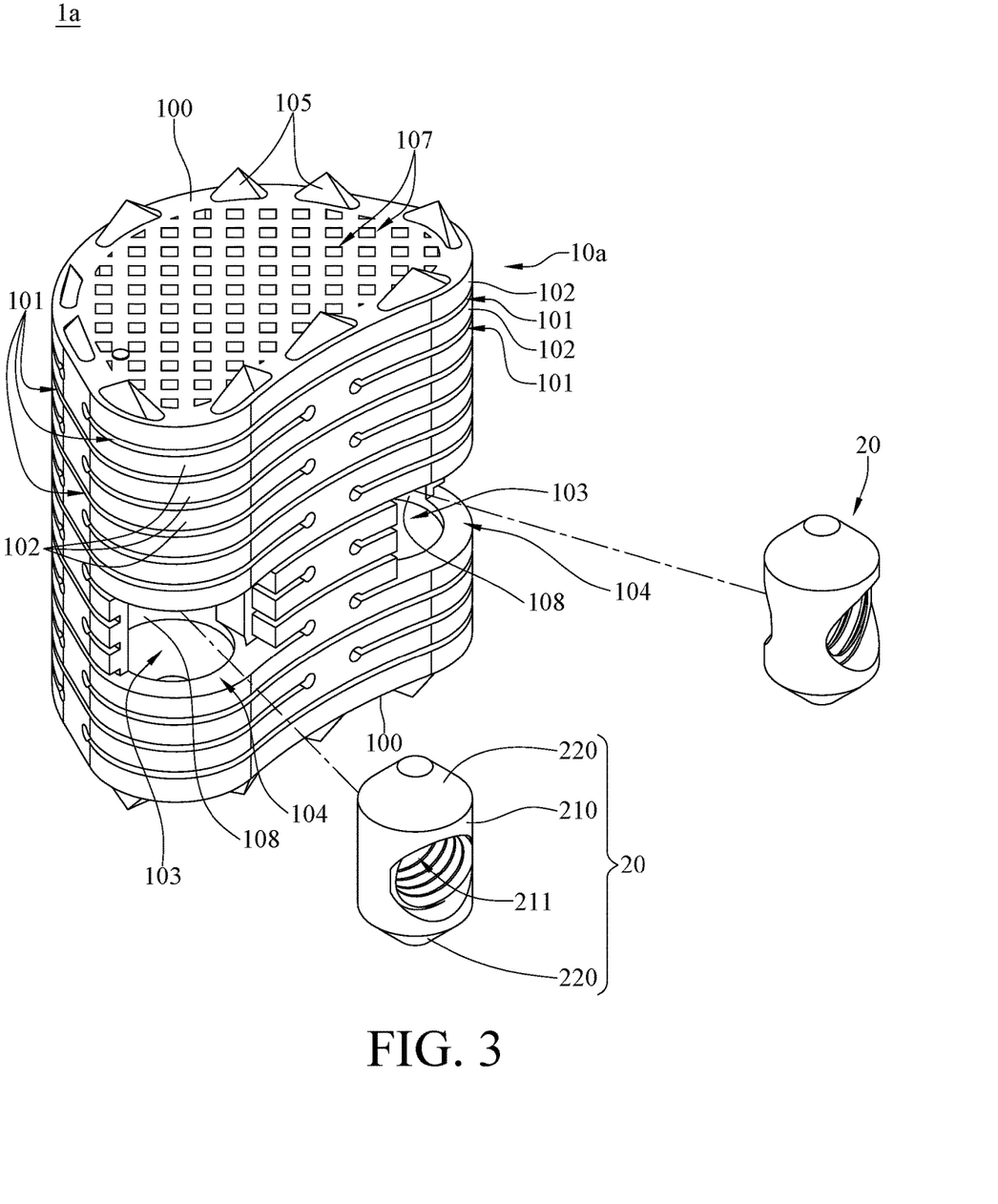
FIG. 3 is an exploded perspective view of the vertebral body implant in FIG. 2.
Figure 4:
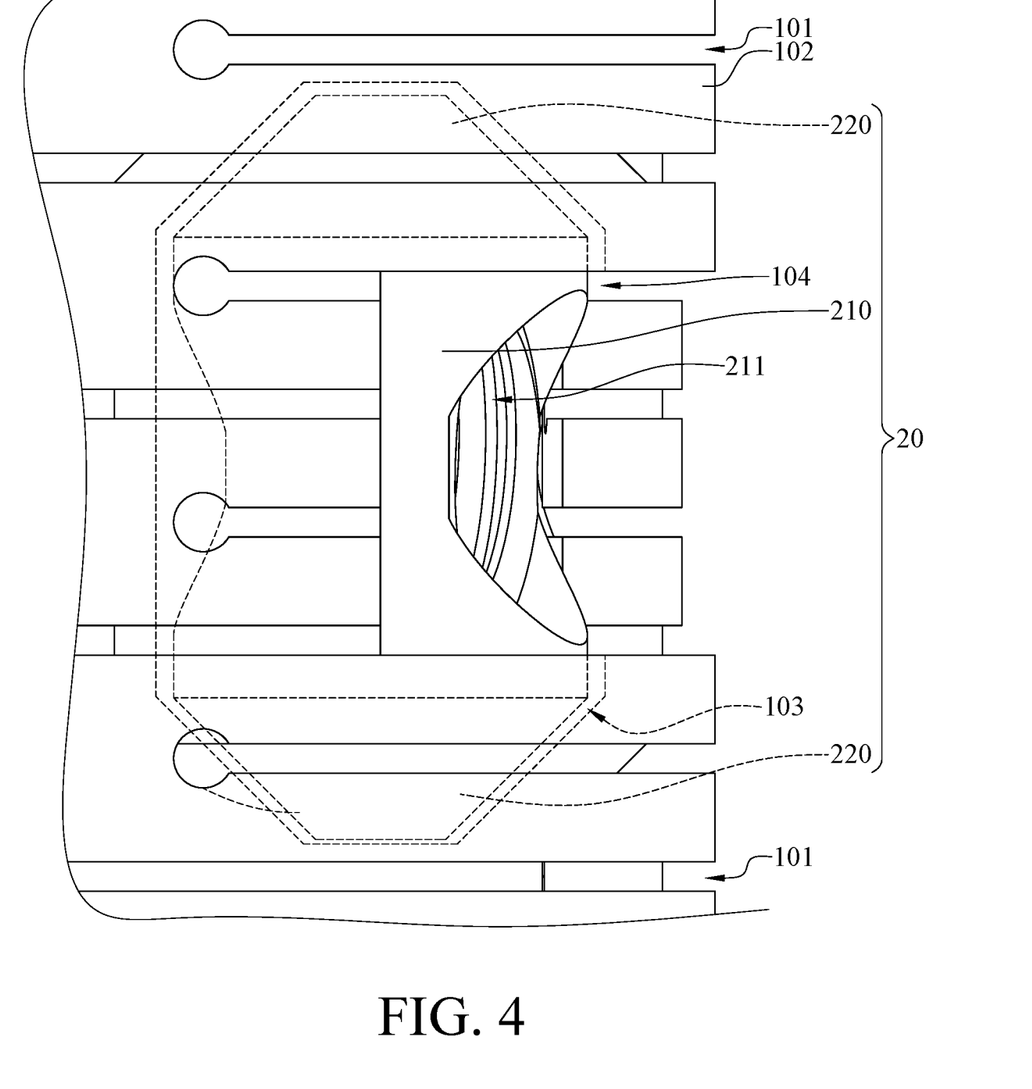
FIG. 4 is a partial enlarged view of the vertebral body implant in FIG. 2.

In detail, please refer to FIGS. 2-4, FIG. 2 is a side view of the vertebral body implant 1a in FIG. 1, FIG. 3 is an exploded perspective view of the vertebral body implant 1a in FIG. 2, and FIG. 4 is a partial enlarged view of the vertebral body implant 1a in FIG. 2. In this and some other embodiments, the vertebral body implant 1a at least includes a flexible main body 10a and two pedicle screw joints 20. The flexible main body 10a is substantially an irregular shaped column and is an integrally formed single piece. The flexible main body 10a has two opposite bone contact surfaces 100 respectively configured to engage with the adjacent vertebral bodies (e.g., the vertebral bodies 91 shown in FIG. 1).

It is understood that the vertebral body has hard outer layer of bones composed of cortical bone and soft inner layer of bones composed of cancellous bone. Regarding this composition of the vertebral body, in this and some other embodiments, the flexible main body 10a may have a customized shape and size matching the contour of the adjacent vertebral bodies so that the bone contact surfaces 100 at least reach the range of the cortical bone of the vertebral bodies. As such, the stress from the vertebral body implant 1a would be uniformly distributed on the vertebral bodies so that the stress concentration on the inner soft cancellous bone of the vertebral bodies is effectively minimized.

In addition, the configuration of the flexible main body 10a gives itself the ability of compressibility, elasticity, and flexibility. As shown, the flexible main body 10a has a plurality of slots 101 spaced apart from one another, such that the flexible main body 10a has a plurality of deformable portions 102 which are spaced by a given distance (i.e., the slot 101). From the viewpoint of FIG. 2, the deformable portions 102 is located above another deformable portion 102, thus when a certain amount of force is applied on the deformable portions 102, the deformable portions 102 can be deformed or slightly bend with respect to the nearby deformable portions 102.

In addition, in some embodiments, regarding the arrangement of the slots 101, the slots 101 in each layer at least occupies approximately 50-99% of the perimeter of the flexible main body 10a in the same layer, and the slots 101 of the adjacent layers may have a phase difference of approximately 0-180 degrees with respect to the central line of the flexible main body 10a, but the disclosure is not limited thereto. Note that the arrangement, length, and size of the slots on the flexible main body all may be modified according to actual requirements.

In addition, to aid the fusion process and prevent the flexible main body 10a from slipping out of place, in this or some other embodiments, the flexible main body 10a further has a plurality of tooth portions 105 protruding from the bone contact surfaces 100 and configured to engage with the adjacent vertebral bodies 91. Also, as shown in FIG. 3, in this and some other embodiments, the tooth portions 105 are arranged along the contour of the bone contact surfaces 100, thus it is understood that the tooth portions 105 are used to engage with the outer hard cortical bone of the vertebral bodies. As such, the tooth portions 105 are prevented from damaging the inner soft cancellous bone of the vertebral bodies, and which also helps to reduce the stress concentration on the inner soft cancellous bone of the vertebral bodies.

However, the arrangement of the tooth portions 105 on the bone contact surfaces 100 is not restricted. In some other embodiments, the tooth portions 105 on the bone contact surface 100 may be arranged in array or in random manner. In addition, each of the tooth portions 105 may be in height of approximately 0.5-3 millimeters, and its inclined surfaces may be at approximately 20-70 degrees to the bone contact surfaces 100, but these values are not restricted and may be modified according to actual requirements.

In addition, in this or some other embodiments, the flexible main body 10a may have pores 107, and the pores 107 allow the nearby tissues to grow into the vertebral body implant 1a to aid the fusion process. The pores 107 may be distributed over part of or the whole of the flexible main body 10a, such that the vertebral body implant 1a may have a porosity of approximately 20%-80%.

Note that the size and shape of the pores 107 and the distance among the pores 107 are not restricted and may be modified according to actual requirements. In some embodiments, the pores 107 may be in grid shape or irregular holes in a sponge. Further, the quantity of the pores 107 in portions of the flexible main body 10a may also be modified; that is, some portions of the flexible main body 10a may be much denser than the other portions of the flexible main body 10a. However, for the purpose of simple and clear illustration, the pores 107 may only be illustrated on the bone contact surfaces 100.

In this and some other embodiments, the flexible main body 10a is also configured for the installation of at least two pedicle screw joints 20. Specifically, as shown, the flexible main body 10a further has at least two joint-accommodating holes 103, the pedicle screw joints 20 are respectively movably accommodated in the joint-accommodating holes 103. In detail, the flexible main body 10a has two openings 104 respectively located at different sides of the flexible main body 10a, and each of the openings 104 are formed between two of the deformable portions 102, the joint-accommodating holes 103 are respectively exposed from the openings 104, such that each of the pedicle screw joints 20 is partially exposed from the opening 104 but the other part of the pedicle screw joints 20 are hidden in the flexible main body 10a. In other words, the height and width of the pedicle screw joint 20 are larger than the height and width of the opening 104.

Further, the vertebral body implant 1a may be 3D printed in the same step; that is, the flexible main body 10a and the pedicle screw joints 20 were 3D printed together at the same time. Therefore, when the flexible main body 10a and the pedicle screw joints 20 are formed, they also self-assemble to become the vertebral body implant 1a shown in FIG. 2. Specifically, the pedicle screw joints 20 are formed in the joint-accommodating holes 103 of the flexible main body 10a during the formation of the flexible main body 10a. Therefore, after the flexible main body 10a and the pedicle screw joints 20 had been formed, the pedicle screw joints 20 were already existing in the flexible main body 10a, such that the pedicle screw joints 20 are unable to be directly removed from the joint-accommodating holes 103 via the openings 104. Herein, it is understood that the pedicle screw joint 20 is also an integrally formed single piece.

The pedicle screw joint 20 is configured for the installation of the aforementioned pedicle screw 81. The pedicle screw 81 can be movably disposed on the flexible main body 10a via the pedicle screw joint 20. In detail, in this and some other embodiments, the pedicle screw joint 20 at least includes a main portion 210 and at least two embedded portions 220. The main portion 210 is connected to and located between the embedded portions 220. The embedded portion 220 is configured to be embedded into the joint-accommodating hole 103 of the flexible main body 10a and completely hidden in the flexible main body 10a. The main portion 210 is the portion of the pedicle screw joint 20 that is partially exposed from the opening 104.

In this embodiment, the embedded portions 220 of the pedicle screw joint 20 may be in a cone shape, correspondingly, the joint-accommodating hole 103 may have conical-shaped recesses (not numbered) for accommodating the embedded portions 220. This arrangement allows the pedicle screw joint 20 to be rotatable in the flexible main body 10a. However, the shapes of the pedicle screw joint and the mating hole for the joint are not restricted. In some other embodiments, the pedicle screw joint may be a spherical object, correspondingly, the joint-accommodating hole may be a spherical hole for accommodating the pedicle screw joint; in such a case, the pedicle screw joint is allowed to perform multi-directional rotational movement with respect to the flexible main body. Alternatively, in another embodiment, the pedicle screw joint may have a columnar protrusion rotatably located in the hole in the joint-accommodating hole; in such an arrangement, the pedicle screw joint is still able to rotate in the joint-accommodating hole, and, in such a case, the opening of the flexible main body may substantially have the same height and width as that of the pedicle screw joint.

In this and some other embodiments, the main portion 210 is the part of the pedicle screw joint 20 for the engagement with the pedicle screw 81. As shown, the main portion 210 has a screw hole 211 configured for the insertion of the pedicle screw 81. As such, the pedicle screw 81 can be movably disposed on the flexible main body 10a by engaging with the pedicle screw joint 20, such that the surgeon is allowed to easily adjust the angle of the pedicle screw 81. In some embodiments, the vertebral body implant 1a may enable the pedicle screw 81 to have an angle adjustment range of approximately 0-150 degrees. Note that the location of the pedicle screw joint 20 on the flexible main body 10a is not restricted and may be modified according to actual requirements.

Furthermore, in this and some other embodiments, the screw hole 211 of the main portion 210 of the pedicle screw joint 20 is a through hole, and the flexible main body 10a further has at least one screw contact inner wall 108 located in the joint-accommodating hole 103 and can be exposed from the screw hole 211 and the opening 104 of the flexible main body 10a. As such, when the pedicle screw 81 screwed into the pedicle screw joint 20 is positioned to the required angle, the surgeon can further screw the pedicle screw 81 into the joint-accommodating hole 103 to make it press against the screw contact inner wall 108 behind the pedicle screw joint 20, by doing so, the tight contact between the pedicle screw 81 and the screw contact inner wall 108 forces the pedicle screw joint 20 to press against the inner wall of the joint-accommodating hole 103 nearby the opening 104, such that the pedicle screw 81 is fixed in the current angle.

Figure 5:
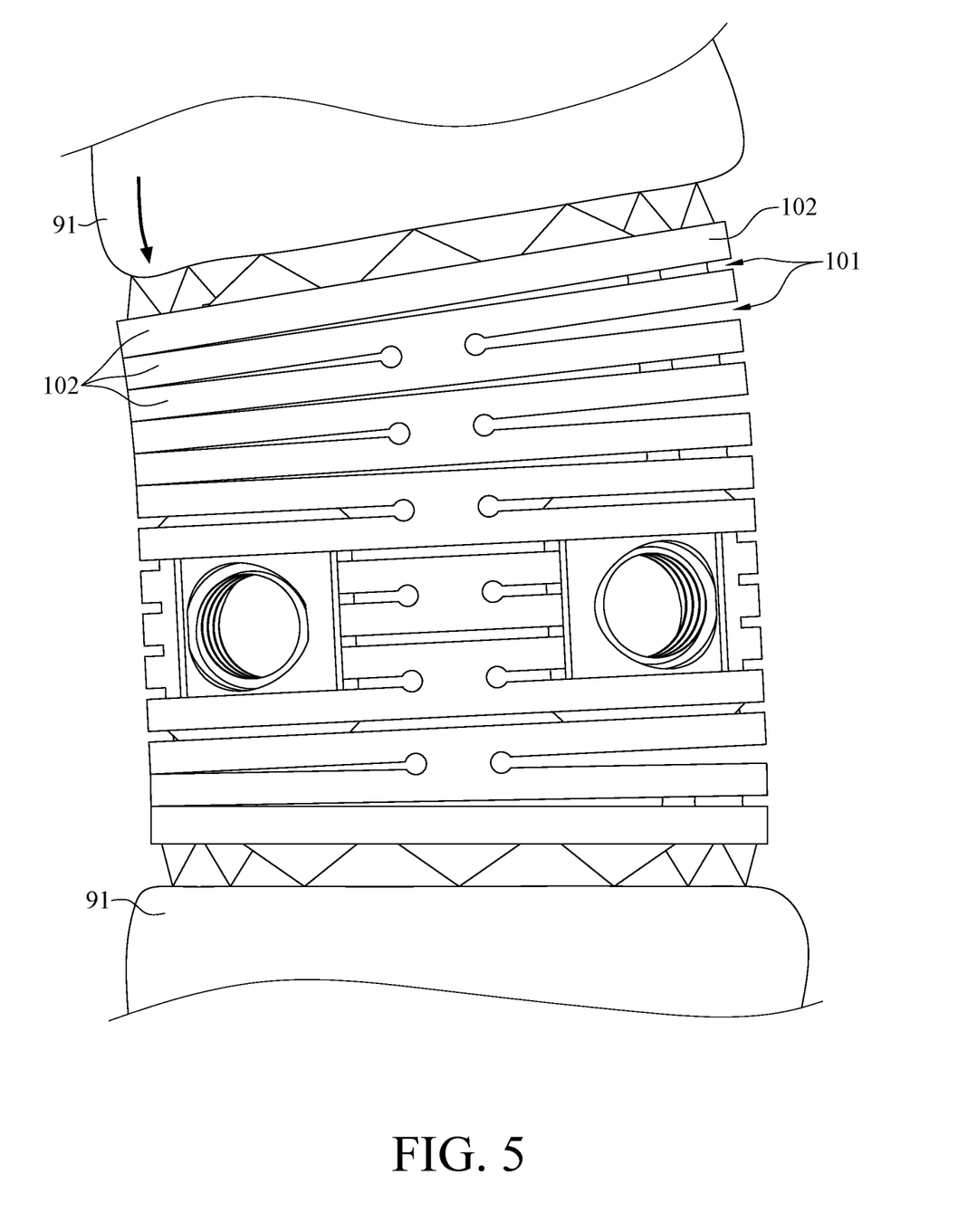
FIG. 5 depicts a side view of the vertebral body implant in FIG. 1 during loading.

Then, please refer to FIG. 5, FIG. 5 depicts a side view of the vertebral body implant 1a in FIG. 1 during loading. For the purpose of simple and clear illustration, the pedicle screw 81 is omitted from FIG. 5. As shown, the vertebral body implant 1a has sufficient rigidity to provide proper support to the vertebral body 91 and maintain the desired position of the vertebral body 91, meanwhile, the deformable portions 102 of the vertebral body implant 1a are able to be deformed along with the motion of the vertebral bodies 91 during the movement of the spine. This reaction of the vertebral body implant 1a can effectively reduce and absorb the stress and impact from the adjacent vertebral bodies 91 so as to effectively minimize the stress concentration on the vertebral bodies 91, such that the vertebral body implant 1a would not result in lesion or degeneration of the vertebral bodies 91 and the vertebral body implant 1a would not shift or slip out of place. According to simulation results, the vertebral body implant 1a at least has flexibility of approximately 0-20 degrees in four different directions and has a compressible range of approximately 3 millimeters.

Figure 6:
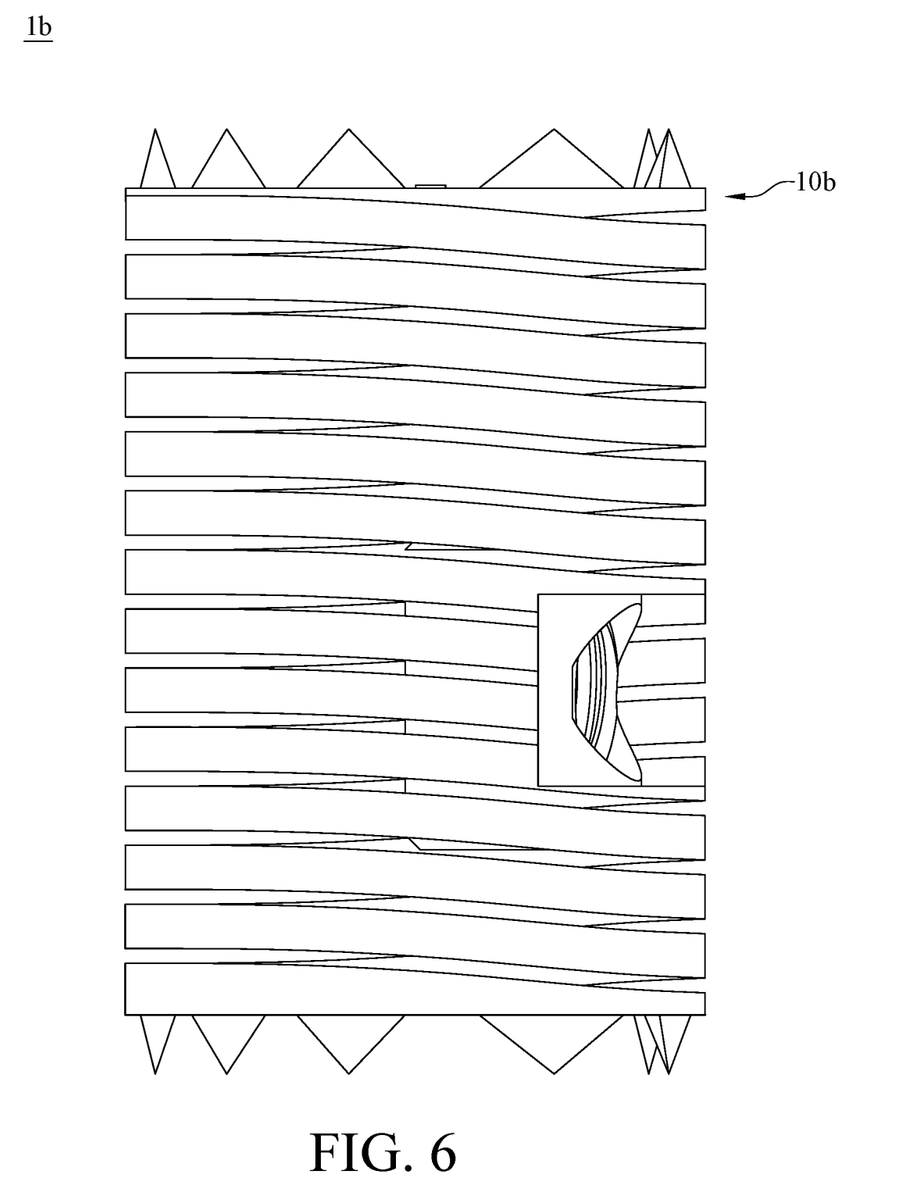
FIG. 6 is a side view of a vertebral body implant according to another embodiment of the disclosure.

Note that the vertebral body implant 1a is merely an exemplary embodiment of the disclosure, and the disclosure is not limited thereto. Then, please refer to FIG. 6, where FIG. 6 is a side view of a vertebral body implant 1b according to another embodiment of the disclosure. For the purpose of simple description, only the differences between this and the previous embodiments will be illustrated below, and the same and similar parts can be obtained with the reference of the aforementioned discussions.

As shown in FIG. 6, in this embodiment, a flexible main body 10b of the vertebral body implant 1b is an integrally formed helix structure, and the form of the flexible main body 10b offers a certain degree of flexibility and compressibility in multi directions. As such, the vertebral body implant 1b is also able to effectively minimize the stress concentration and prevent itself from shifting and slipping out of place. However, the configuration of the flexible main body 10b is not restricted and may be further modified according to actual requirements. In some other embodiments, the flexible main body may merely be a columnar object full of the aforementioned pores 107, and the porosity of the flexible main body is at a level capable of making it achieve the required flexibility and compressibility.

Figure 7A:
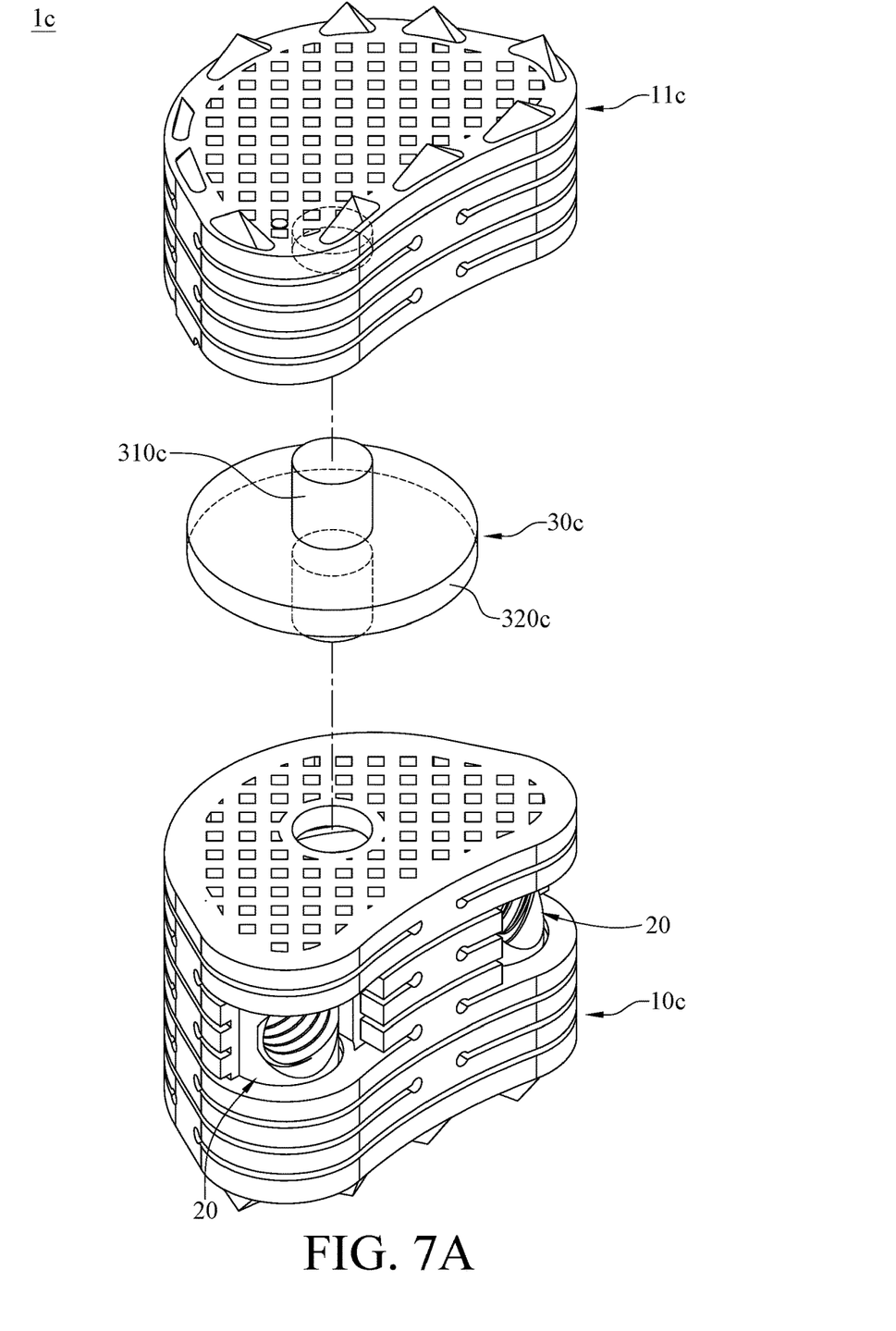
FIG. 7A is an exploded perspective view of a vertebral body implant according to still another embodiment of the disclosure.
Figure 7B:
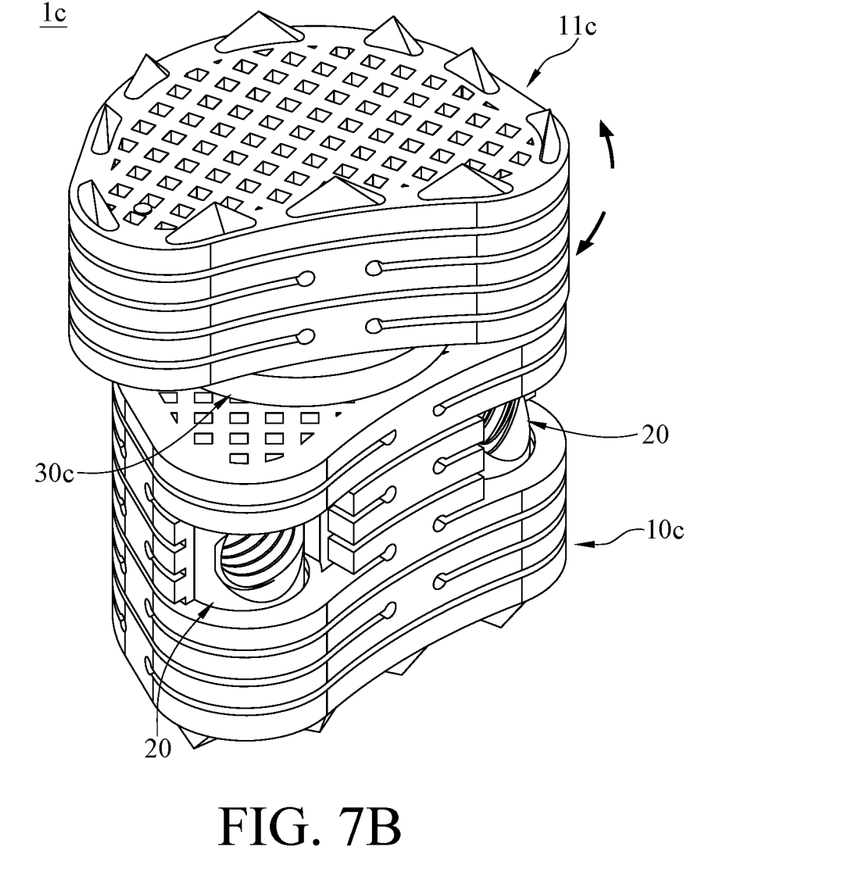
FIG. 7B depicts the usage of the vertebral body implant in FIG. 7A.

Alternatively, please refer to FIGS. 7A-7B, wherein FIG. 7A is an exploded perspective view of a vertebral body implant 1c according to still another embodiment of the disclosure, and FIG. 7B depicts the usage of the vertebral body implant 1c in FIG. 7A. For the purpose of simple description, only the differences between this and the previous embodiments will be illustrated below, and the same and similar parts can be obtained with the reference of the aforementioned discussions.

As shown, in this embodiment, the vertebral body implant 1c includes two independent flexible main bodies: a first flexible main body 10c and a second flexible main body 11c. The first flexible main body 10c and the second flexible main body 11c may have the same or similar configuration to the flexible main body of the previous embodiment, so the same and similar parts will not be repeated hereinafter.

The vertebral body implant 1c further includes a connecting component 30c. The first flexible main body 10c and the second flexible main body 11c are respectively pivotably connected to two opposite sides of the connecting component 30c. Specifically, in this embodiment, the connecting component 30c includes a shaft portion 310c and a spacer portion 320c, where the spacer portion 320 may be in a plate shape. The shaft portion 310c is disposed on the spacer portion 320. The first flexible main body 10c and the second flexible main body 11c are respectively rotatably disposed on two opposite ends of the shaft portion 310c. Note that the connecting component 30c may also be an integrally formed single piece, and the first flexible main body 10c and the second flexible main body 11c may be directly sleeved on the shaft portion 310c.

In such an arrangement, the first flexible main body 10c and the second flexible main body 11c both have a certain degree of flexibility and compressibility in multi directions, meanwhile, the first flexible main body 10c and the second flexible main body 11c are allowed to rotate with respect to each other, such that the vertebral body implant 1c is able to cooperate a larger twist angle of the vertebral bodies, as the arrows shown in FIG. 7B. Herein, considering that the first flexible main body 10c and the second flexible main body 11c may constantly have friction with the connecting component 30c, the connecting component 30c may be made of durable material, such as polymer or ceramic.

Figure 8A:
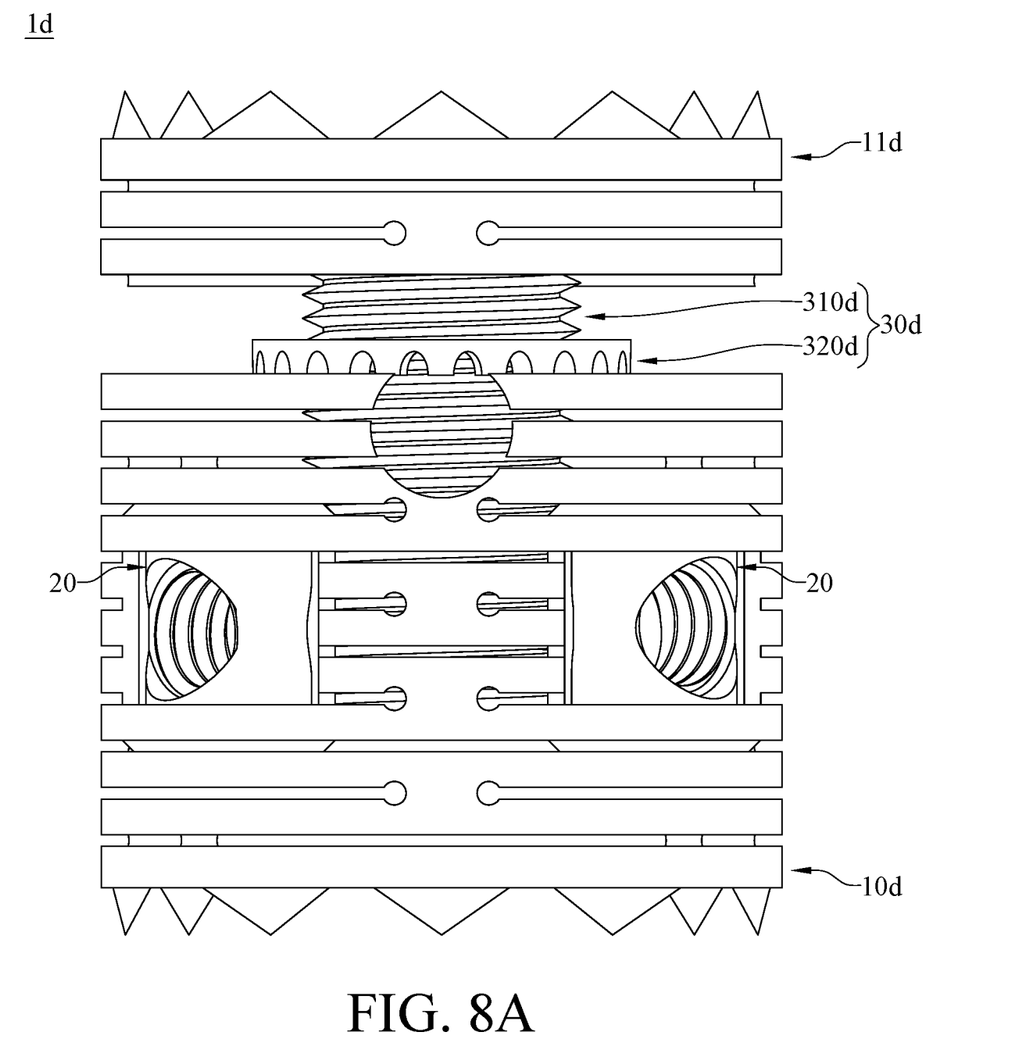
FIG. 8A is a perspective view of a vertebral body implant according to still yet another embodiment of the disclosure.
Figure 8B:
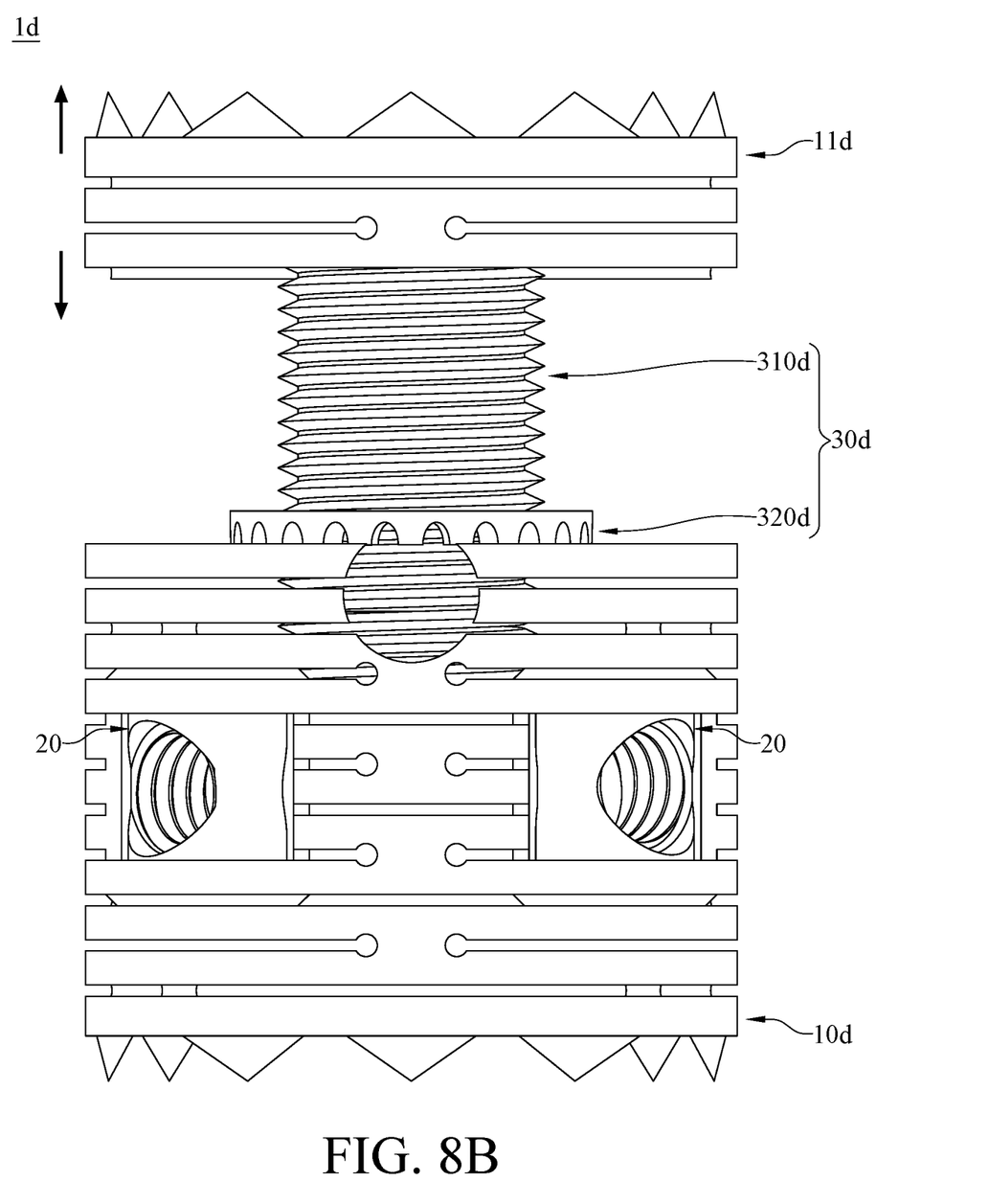
FIG. 8B depicts the usage of the vertebral body implant in FIG. 8A.

Alternatively, please refer to FIGS. 8A-8B, where FIG. 8A is a perspective view of a vertebral body implant 1d according to still yet another embodiment of the disclosure, and FIG. 8B depicts the usage of the vertebral body implant 1d in FIG. 8A. For the purpose of simple description, only the differences between this and the previous embodiments will be illustrated below, and the same and similar parts can be obtained with the reference of the aforementioned discussions.

As shown, in this embodiment, a shaft portion 310d of a connecting component 30d of the vertebral body implant 1d is a screw rod, the shaft portion 310d is screwed into a first flexible main body 10d and is fixed to a second flexible main body 11d which is spaced apart from the first flexible main body 10d, a spacer portion 320d of the connecting component 30d is located between the first flexible main body 10d and the second flexible main body 11d and is fixed to the first flexible main body 10d, and the shaft portion 310d is disposed through the spacer portion 320d.

In such an arrangement, the first flexible main body 10d and the second flexible main body 11d both have a certain degree of flexibility and compressibility in multi directions, meanwhile, the distance between the first flexible main body 10d and the second flexible main body 11d is adjustable by the connecting component 30d. As such, the height of the vertebral body implant 1d can be adjusted according to the required height of the space between the adjacent vertebral bodies. As the arrows shown in FIG. 8B, the second flexible main body 11d is able to move toward or away from the first flexible main body 10d along the shaft portion 310d of the connecting component 30d. In some embodiments, the vertebral body implant 1d may have a height adjustment range of approximately 20-100 millimeters or have a height adjustment range approximately 10-80% of the original height.

According to the vertebral body implant as discussed in the above embodiments of the disclosure, since the flexible main body is made of a single piece, the vertebral body implant has sufficient rigidity to maintain the distance between the adjacent vertebral bodies while possessing sufficient flexibility and compressibility for the motion of the vertebral bodies. Therefore, the vertebral body implant is not only able to reduce or absorb the pressure applied to the vertebral body but also able to effectively minimize the stress concentration on the vertebral bodies to avoid causing damage to them. As a result, the vertebral body implant of the disclosure would not result in lesion or degeneration of the vertebral bodies and would not slip out of place, preventing fusion failure.

Also, the pedicle screw joint, made of a single piece, is movably located in the flexible main body, which enables the surgeon to adjust the angle of the pedicle screw during the implantation.

It will be apparent to those skilled in the art that various modifications and variations can be made to the present disclosure. It is intended that the specification and examples be considered as exemplary embodiments only, with a scope of the disclosure being indicated by the following claims and their equivalents.

What is claimed is:

1. A vertebral body implant, comprising:
a flexible main body, being an integrally formed single piece having at least one joint-accommodating hole and at least one opening connected to the at least one joint-accommodating hole; and
at least one pedicle screw joint, being an integrally formed single piece movably accommodated in the at least one joint-accommodating hole;
wherein the at least one pedicle screw joint comprises a cylindrical main portion partially exposed from the opening and two tapered embedded portions on opposite sides of the cylindrical main portion, the two tapered embedded portions tapering away from the cylindrical main portion.

2. The vertebral body implant according to claim 1, wherein the at least one pedicle screw joint comprises a main portion and two embedded portions, the main portion is located between the embedded portions, the embedded portions are hidden in the flexible main body, and the main portion has a screw hole exposed from the at least one opening.

3. The vertebral body implant according to claim 2, wherein the flexible main body has at least one screw contact inner wall, the at least one screw contact inner wall is located in the at least one joint-accommodating hole and is exposed from the screw hole of the main portion and the at least one opening.

4. The vertebral body implant according to claim 1, wherein the flexible main body and the at least one pedicle screw joint were 3D printed together.

5. The vertebral body implant according to claim 1, wherein the flexible main body has a plurality of slots spaced apart from one another.

6. The vertebral body implant according to claim 1, wherein the flexible main body is an integrally formed helix structure.

7. The vertebral body implant according to claim 1, wherein the flexible main body has two bone contact surfaces and a plurality of tooth portions, the plurality of tooth portions protrude from the bone contact surfaces and are arranged along contours of the bone contact surfaces.

8. The vertebral body implant according to claim 1, further comprising a connecting component and another flexible main body, the flexible main body and the another flexible main body are rotatably connected to each other via the connecting component.

9. The vertebral body implant according to claim 8, wherein the connecting component comprises a shaft portion and a spacer portion, the flexible main body and the another flexible main body are respectively rotatably disposed on two opposite ends of the shaft portion, the shaft portion is fixed on the spacer portion, the spacer portion is located between and clamped by the flexible main body and the another flexible main body.

10. The vertebral body implant according to claim 8, wherein the connecting component comprises a shaft portion and a spacer portion, the shaft portion is partially screwed into the flexible main body, and the shaft portion is fixed to the another flexible main body, the shaft portion is movably disposed through the spacer portion, the spacer portion is located between the flexible main body and the another flexible main body.

* * * * *